United States Patent
Takashima

(10) Patent No.: US 12,254,974 B2
(45) Date of Patent: Mar. 18, 2025

(54) MEDICINE COLLATION DEVICE, MEDICINE COLLATION SYSTEM, MEDICINE MANAGEMENT METHOD, AND PROGRAM

(71) Applicant: FUJIFILM Toyama Chemical Co., Ltd., Tokyo (JP)

(72) Inventor: Masanobu Takashima, Kanagawa (JP)

(73) Assignee: FUJIFILM Medical Co., Ltd., Tokyo (JP)

(*) Notice: Subject to any disclaimer, the term of this patent is extended or adjusted under 35 U.S.C. 154(b) by 301 days.

(21) Appl. No.: 17/709,898

(22) Filed: Mar. 31, 2022

(65) Prior Publication Data

US 2022/0223262 A1 Jul. 14, 2022

Related U.S. Application Data

(63) Continuation of application No. PCT/JP2020/035969, filed on Sep. 24, 2020.

(30) Foreign Application Priority Data

Oct. 1, 2019 (JP) .................................. 2019-181310

(51) Int. Cl.
   *G16H 30/40* (2018.01)
   *G06V 10/762* (2022.01)
   (Continued)

(52) U.S. Cl.
   CPC ........... *G16H 30/40* (2018.01); *G06V 10/762* (2022.01); *G16H 20/10* (2018.01); *G16H 30/20* (2018.01)

(58) Field of Classification Search
   CPC ......... G16H 30/40; G16H 30/20; G06H 20/10
   See application file for complete search history.

(56) References Cited

U.S. PATENT DOCUMENTS

2013/0114870 A1 5/2013 Mardirossian
2013/0194414 A1* 8/2013 Poirier .................. G16H 20/13
                                                              382/128
(Continued)

FOREIGN PATENT DOCUMENTS

CN     105073082 A     11/2015
CN     105338945 A      2/2016
(Continued)

OTHER PUBLICATIONS

International Search Report dated Dec. 15, 2020, issued in International Application No. PCT/JP2020/035969.

(Continued)

*Primary Examiner* — Dhaval V Patel
(74) *Attorney, Agent, or Firm* — Sughrue Mion, PLLC

(57) ABSTRACT

To provide a medicine collation device, a medicine collation system, a medicine management method, and a program, capable of collecting medicine images that are candidates for master images. The medicine collation device includes: a medicine image acquiring unit configured to acquire a medicine image generated by imaging a medicine to be collated; a first master image storing unit configured to store a master image of the medicine; a collating unit configured to collate the medicine image with the master image; an associating unit configured to associate the medicine image collated by the collating unit, with identification information on the medicine image; and a transmitting unit configured to transmit the medicine image and the identification information that are associated in the associating unit, to an outside.

12 Claims, 14 Drawing Sheets

(51) Int. Cl.
  G16H 20/10 (2018.01)
  G16H 30/20 (2018.01)

(56) References Cited

U.S. PATENT DOCUMENTS

| | | | |
|---|---|---|---|
| 2014/0002631 A1 | 1/2014 | Amano et al. | |
| 2015/0170373 A1* | 6/2015 | Yonaha | G16H 10/60 382/143 |
| 2015/0178674 A1* | 6/2015 | Yonaha | G06Q 10/087 705/2 |
| 2016/0005160 A1* | 1/2016 | Ito | G16H 20/10 348/86 |
| 2016/0104282 A1 | 4/2016 | Takahashi | |
| 2016/0114925 A1 | 4/2016 | Yuyama et al. | |
| 2017/0264867 A1 | 9/2017 | Amano et al. | |
| 2017/0305589 A1* | 10/2017 | Yuyama | B65B 35/14 |
| 2019/0050977 A1 | 2/2019 | Segawa | |
| 2019/0051396 A1 | 2/2019 | Hasegawa | |
| 2019/0377977 A1 | 12/2019 | Iwami et al. | |
| 2020/0151490 A1 | 5/2020 | Iwami | |
| 2020/0156120 A1 | 5/2020 | Amano et al. | |
| 2020/0175318 A1 | 6/2020 | Yokouchi et al. | |
| 2020/0175319 A1 | 6/2020 | Yokouchi | |

FOREIGN PATENT DOCUMENTS

| | | | | |
|---|---|---|---|---|
| CN | 109069345 A | | 12/2018 | |
| CN | 109074860 A | | 12/2018 | |
| JP | 2010-165159 A | | 7/2010 | |
| JP | 2012-008942 A | | 1/2012 | |
| JP | 2016-126361 A | | 7/2016 | |
| JP | 2017127407 A | * | 7/2017 | ............ G06F 17/30 |
| KR | 10-2017-0110268 A | | 10/2017 | |
| WO | 2015/152225 A1 | | 10/2015 | |
| WO | WO-2018173649 A1 | * | 9/2018 | ............... A61J 1/03 |
| WO | 2018/190394 A1 | | 10/2018 | |
| WO | 2019/039300 A1 | | 2/2019 | |

OTHER PUBLICATIONS

Written Opinion dated Dec. 15, 2020, issued in International Application No. PCT/JP2020/035969.
International Preliminary Report on Patentability dated Apr. 5, 2022, issued in International Application No. PCT/JP2020/035969.
Office Action issued Nov. 13, 2023 in European Application No. 20 872 754.5.
Japanese Office Action dated Apr. 19, 2023 in Japanese Application No. 2021-550675.
Japanese Office Action dated Aug. 18, 2023 in Japanese Application No. 2021-550675.
Extended European Search Report dated Oct. 12, 2022 in European Application No. 20872754.5.
Chinese Office Action dated Jul. 11, 2024 in Application No. 202080067253.4.
Communication dated Sep. 13, 2024 issued by the European Patent Office in application No. 20872754.5.
Communication dated Mar. 26, 2024, issued in Chinese Application No. 202080067253.4.

* cited by examiner

FIG.7

| MEDICINE NAME | ATTRIBUTE INFORMATION | MASTER IMAGE (FRONT) | MASTER IMAGE (BACK) |
|---|---|---|---|
| T₁ | MEDICINE CODE :XXX-XXXX<br>MEDICINE TYPE :TABLET<br>SHAPE :SPHEROIDAL<br>SIZE :10 MM IN DIAMETER<br>COLOR :WHITE COLOR<br>ENGRAVED MARK :133 | (133) | ( ) |

MEDICINE COLLATION DEVICE, MEDICINE COLLATION SYSTEM, MEDICINE MANAGEMENT METHOD, AND PROGRAM

CROSS-REFERENCE TO RELATED APPLICATIONS

The present application is a Continuation of PCT International Application No. PCT/JP2020/035969 filed on Sep. 24, 2020 claiming priority under 35 U.S.C § 119(a) to Japanese Patent Application No. 2019-181310 filed on Oct. 1, 2019. Each of the above applications is hereby expressly incorporated by reference, in its entirety, into the present application.

BACKGROUND OF THE INVENTION

1. Field of the Invention

The present invention relates to a medicine collation device, a medicine collation system, a medicine management method, and a program.

2. Description of the Related Art

Conventionally, various kinds of devices that recognize types of medicines have been proposed or provided. For example, the types of the medicines are recognized by imaging a medicine to be recognized and collating the medicine image with master images of medicines registered in advance.

International Publication No. WO 2018/173649 (hereinafter referred to as "PTL 1") discloses a medicine recognition device that collates a medicine image with master images to perform medicine discrimination. The device disclosed in PTL 1 acquires information on a position of a medicine based on the medicine image and updates a master image when the position of the medicine satisfies a prescribed condition.

CITATION LIST

Patent Literature 1: International Publication No. WO 2018/173649

SUMMARY OF THE INVENTION

Master images are essential for improving accuracy in image recognition of medicines. However, a total of over 8,000 types of medicines, such as tablet medicines and capsule medicines, are present on the market. For example, there are medicines difficult to obtain, such as expensive medicines. Under these circumstances, it is difficult to obtain medicine images for all the medicines and register them as master images.

The present invention has been made in light of these circumstances, and an object of the present invention is to provide a medicine collation device, a medicine collation system, a medicine management method, and a program, capable of collecting medicine images which are candidates for master images.

In order to accomplish the object, following aspects of the invention are provided.

A medicine collation device according to a first aspect is a medicine collation device, including: a medicine image acquiring unit configured to acquire a medicine image generated by imaging a medicine to be collated; a first master image storing unit configured to store a master image of the medicine; a collating unit configured to collate the medicine image acquired by the medicine image acquiring unit, with the master image stored in the first master image storing unit; an associating unit configured to associate the medicine image collated by the collating unit, with identification information on the medicine image; and a transmitting unit configured to transmit the medicine image and the identification information that are associated in the associating unit, to an outside.

According to the first aspect, the medicine image collated with the master image is associated with the identification information on the medicine image and transmitted to the outside. This makes it possible to use the medicine image associated with the identification information as a candidate for the master image.

The medicine image may include an image extracted from a captured image formed by imaging a plurality of medicines. The medicine image may include a plurality of images imaged from a plurality of directions.

The master image may include a plurality of images imaged from a plurality of directions.

The collating unit may perform audit based on prescription information, or may perform audit without using the prescription information.

In a second aspect relating to the medicine collation device according to the first aspect, the associating unit may be configured to associate the medicine image that is determined to be indeterminable in the collating unit, with the identification information.

According to the second aspect, the medicine image determined to be indeterminable may be associated with the identification information and transmitted to the outside.

In a third aspect, the medicine collation device according to the second aspect may include an identification information input unit configured to input the identification information on the image, wherein the associating unit may be configured to associate the identification information on the medicine image input by the identification information input unit, with the medicine image.

According to the third aspect, the medicine image determined to be indeterminable may be associated with the input identification information.

In a fourth aspect relating to the medicine collation device according to the second aspect, the associating unit may be configured to associate the medicine image that is determined to be indeterminable in the collating unit, with identification information indicating indeterminability.

According to the fourth aspect, as to the medicine image determined to be indeterminable, the medicine image to which the identification information indicating indeterminability is added, may be transmitted to the outside.

In a fifth aspect relating to the medicine collation device according to any one of the second to fourth aspects, the first master image storing unit may be configured to update the master image by using the medicine image that is determined to be indeterminable in the collating unit and the identification information associated with the medicine image.

According to the fifth aspect, the master image may be updated by using the medicine image determined to be indeterminable and the identification information associated with the medicine image. This makes it possible to perform collation of medicines not previously stored in the first master image storing unit.

In a sixth aspect, the medicine collation device according to any one of the first to fifth aspects may further include an imaging condition information acquiring unit configured to acquire imaging condition information on the medicine image, wherein the associating unit may be configured to associate the medicine image with the imaging condition information.

According to the sixth aspect, it becomes possible to use the medicine image, and the identification information and imaging condition information on the medicine image.

In a seventh aspect, the medicine collation device according to any one of the first to sixth aspects may further include a lighting condition information acquiring unit configured to acquire lighting condition information on the medicine image, wherein the associating unit may be configured to associate the medicine image with the lighting condition information.

According to the seventh aspect, it becomes possible to use the medicine image, and the identification information and lighting condition information on the medicine image.

In an eighth aspect relating to the medicine collation device according to any one of the first to seventh aspects, the transmitting unit may be configured to transmit the medicine image that is not associated with the identification information in the associating unit, to the outside.

According to the eighth aspect, it is possible to transmit the medicine image that is not associated with the identification information to the outside.

In a ninth aspect relating to the medicine collation device according to the eighth aspect, the associating unit may be configured not to associate the medicine image that is determined to be indeterminable in the collating unit, with the identification information.

According to the ninth aspect, it is possible to configure the medicine collation device so as not to associate the medicine image with the identification information, for the medicine image determined to be indeterminable.

A medicine collation system according to a tenth aspect is a medicine collation system, including: a server device; a second master image storing unit configured to store a master image; and a medicine collation device configured to collate a medicine image generated by imaging a medicine to be collated with the master image, wherein the medicine collation device includes: a medicine image acquiring unit configured to acquire the medicine image; a first master image storing unit configured to store the master image stored in the second master image storing unit; a collating unit configured to collate the medicine image acquired by the medicine image acquiring unit, with the master image stored in the first master image storing unit; an associating unit configured to associate the medicine image collated by the collating unit, with identification information on the medicine image; and a transmitting unit configured to transmit the medicine image and the identification information that are associated in the associating unit, to the server device.

According to the tenth aspect, the effect similar to that in the first aspect can be achieved.

In the tenth aspect, it is possible to appropriately combine features similar to features defined in the second aspect to the ninth aspect. In that case, the components that implement processing or functions defined in the medicine collation device can be understood as the components of the medicine collation system that implements corresponding processing and functions.

In an eleventh aspect relating to the medicine collation system according to the tenth aspect, the server device may be configured to update the master image stored in the second master image storing unit by using the medicine image and the identification information corresponding to the medicine image that are transmitted from the transmitting unit.

According to the eleventh aspect, it is possible to update the second master image storing unit by applying the medicine image associated with the identification information.

In a twelfth aspect relating to the medicine collation system according to the tenth aspect or the eleventh aspect, the server device may be configured to be communicably connected with the medicine collation device via a network.

According to the twelfth aspect, it is possible to configure a network system including the server device and the medicine collation device.

A medicine management method according to a thirteenth aspect is a medicine management method including: a medicine image acquiring step of acquiring a medicine image generated by imaging a medicine to be collated; a collating step of collating the medicine image acquired in the medicine image acquiring step, with a master image of the medicine stored in a first master image storing unit that stores the master image; an associating processing step of associating the medicine image collated in the collating step, with identification information on the medicine image; and a transmitting step of transmitting the medicine image and the identification information associated in the associating processing step, to the outside.

According to the thirteenth aspect, the effect similar to that in the first aspect can be provided.

In the thirteenth aspect, it is possible to appropriately combine the features similar to the features defined in the second aspect to the ninth aspect, the eleventh aspect, and the twelfth aspect. In that case, the components that implement processing and functions defined in the medicine collation device and the medicine collation system can be understood as the components of the medicine management method that implements corresponding processing and functions.

A program according to a fourteenth aspect is a program causing a computer to implement functions including: a medicine image acquiring function of acquiring a medicine image generated by imaging a medicine to be collated; a collating function of collating the medicine image acquired by the medicine image acquiring function, with a master image of the medicine stored in a first master image storing unit that stores the master image; an associating processing function of associating the medicine image collated by the collating function, with identification information on the medicine image; and a transmitting function of transmitting the medicine image and the identification information associated by the associating processing function, to the outside.

According to the fourteenth aspect, the effect similar to that in the first aspect can be provided.

In the fourteenth aspect, it is possible to appropriately combine the features similar to the features defined in the second aspect to the ninth aspect, the eleventh aspect, and the twelfth aspect. In that case, the components that implement processing and functions defined in the medicine collation device and the medicine collation system can be understood as the components of the program that implements corresponding processing and functions.

According to the present invention, the medicine image collated with the master image is associated with identification information on the medicine image, and then transmitted to the outside. This makes it possible to use the medicine image associated with the identification information as a candidate for the master image.

BRIEF DESCRIPTION OF THE DRAWINGS

FIG. 7 is a schematic diagram of a local database shown in FIG. 3.

DESCRIPTION OF THE PREFERRED EMBODIMENTS

Figure 1:
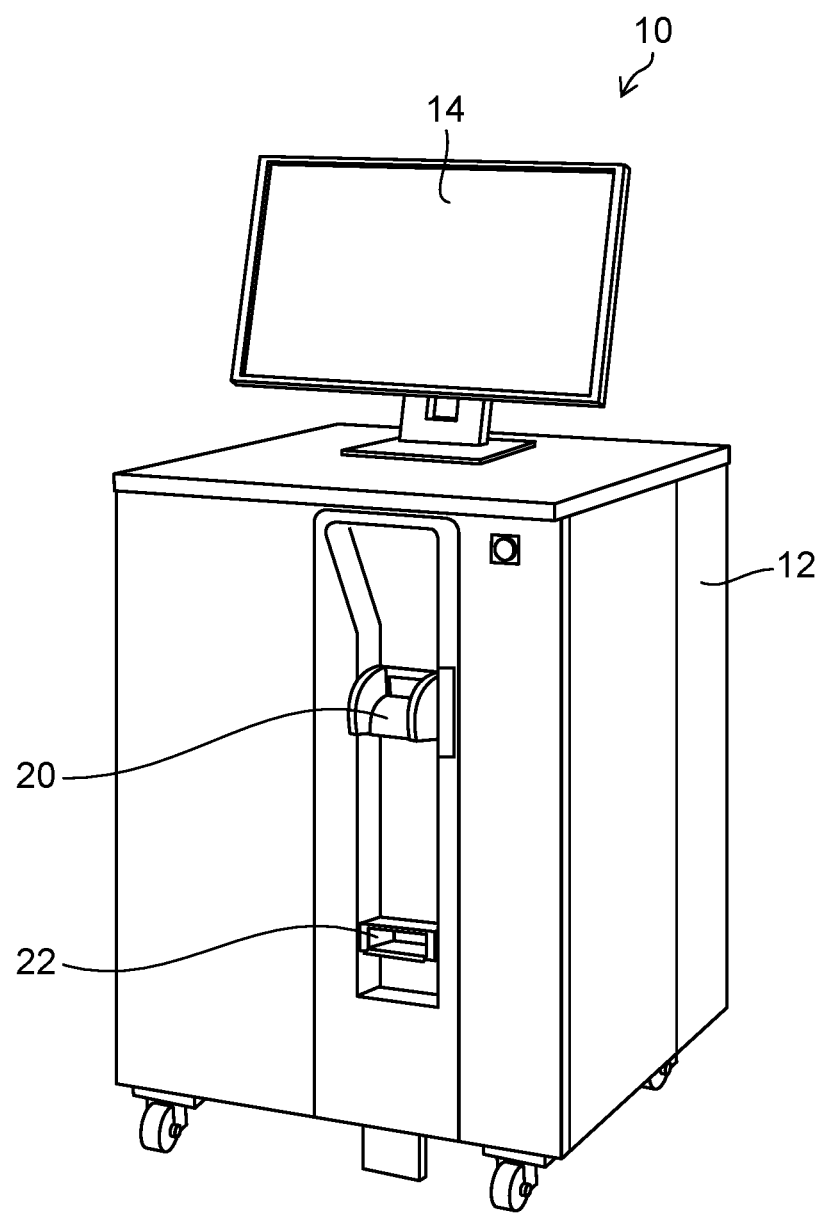
FIG. 1 is a perspective view of a medicine audit device according to an embodiment.

Hereinafter, a preferable embodiment of the present invention is described in detail with reference to accompanying drawings. In this specification, same components are designated by same reference characters, and redundant descriptions are omitted where appropriate.

[Medicine Audit Device]

FIG. 1 is a perspective view of a medicine audit device according to an embodiment. A medicine audit device 10 shown in FIG. 1 performs audit of medicines in one-dose package. Specifically, the medicine audit device 10 automatically determines a type, quantity and the like of each medicine, and collates them with prescription information. The medicine audit device 10 reports an audit result.

The medicine audit device 10 includes a main body 12 and a display device 14. The main body 12 includes an insertion port 20 and a discharge port 22. The insertion port 20 allows insertion of a packaging film in which medicines in one-dose package are enclosed. The insertion port 20 allows insertion of a plurality of packaging films connected in a row. The discharge port 22 allows discharge of the packaging films for which audit is completed. The main body 12 includes a conveying unit that conveys the packaging films from the insertion port 20 to the discharge port 22. Here, in FIG. 1, illustration of the conveying unit is omitted. The conveying unit is designated by reference numeral 18 and illustrated in FIG. 3.

The display device 14 displays various information applied to the medicine audit device 10. For example, the display device 14 displays an audit result display screen showing the audit result. As the display device, a touch panel display device is applied and also used as an operating unit.

The operating unit is operated by an operator to input various information into the medicine audit device 10. Note that the medicine audit device 10 described in the embodiment is equivalent to an example of the medicine collation device.

[Medicine Audit System]

Figure 2:
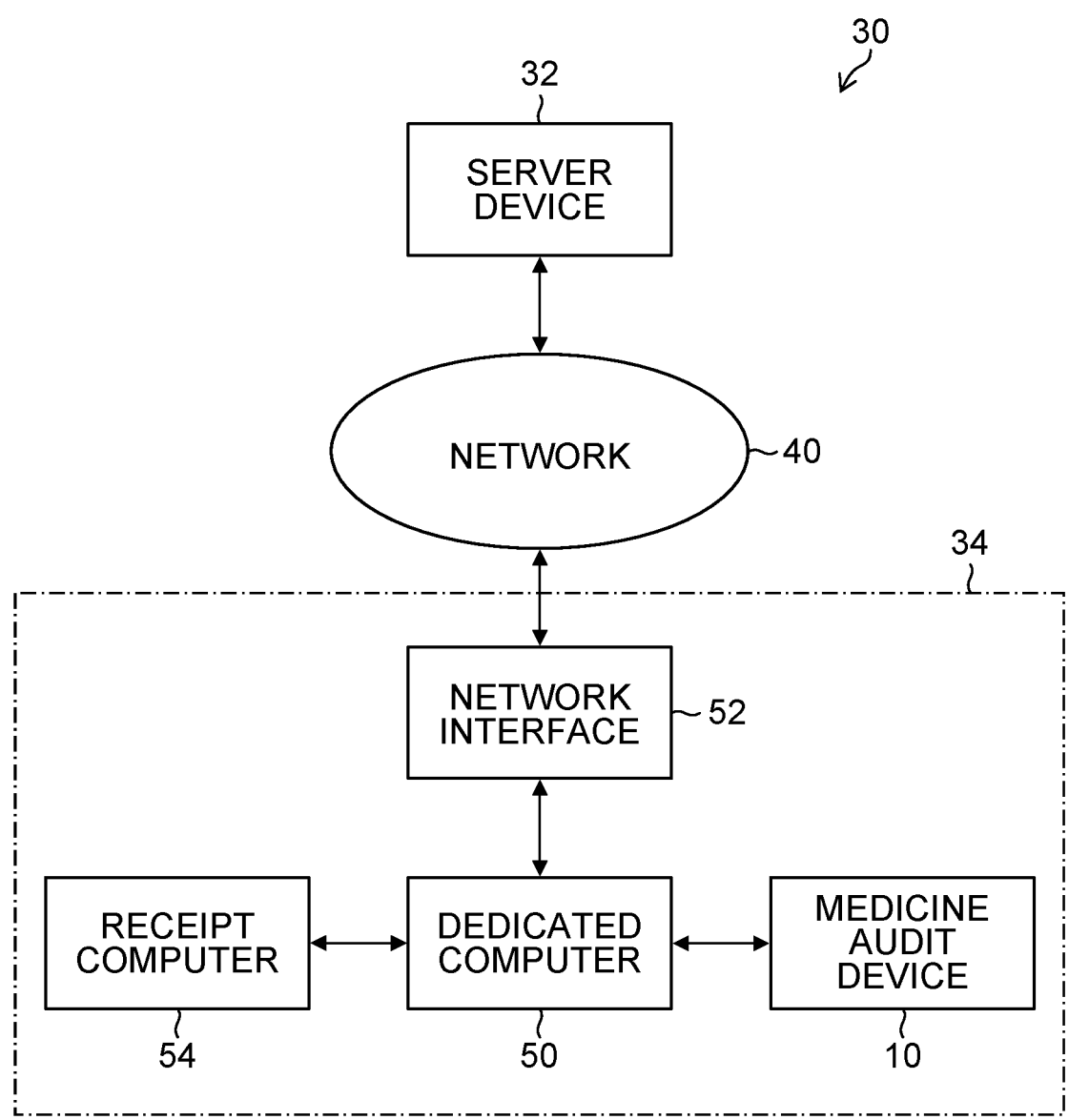
FIG. 2 is a configuration diagram of a medicine audit system according to the embodiment.

FIG. 2 is a configuration diagram of a medicine audit system according to the embodiment. In a medicine audit system 30 shown in FIG. 2, a server device 32 and a client system 34 are communicably connected via a network 40. The medicine audit system 30 may include a plurality of client systems 34.

The server device 32 manages various information regarding medicine audit performed in the client system 34, and provides various information to the client system 34. For the server device 32, cloud computing may be applied.

The client system 34 includes the medicine audit device 10, a dedicated computer 50, a network interface 52, and a receipt computer 54. The client system 34 is communicably connected with the network 40 via the network interface 52.

In the client system 34, the medicine audit device 10 and the receipt computer 54 are connected to the network interface 52 via the dedicated computer 50. The client system 34 may include a storage device such as a hard disk drive. Here, illustration of the storage device is omitted.

As the network 40, a private line may be applied. As the network 40, a public network may be applied. The network 40 can use general purpose communication protocols.

Figure 3:
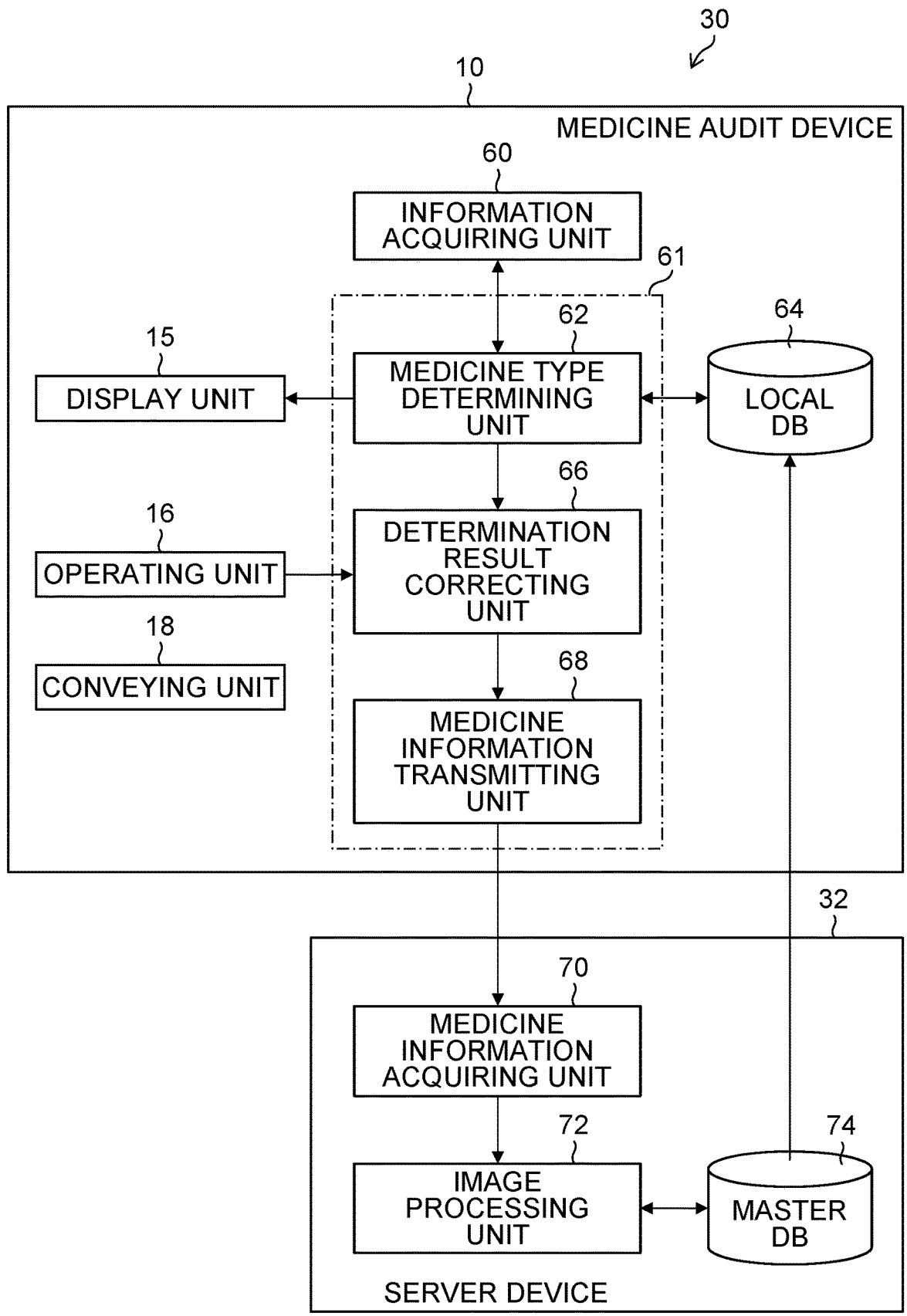
FIG. 3 is a functional block diagram of the medicine audit system shown in FIG. 2.

FIG. 3 is a functional block diagram of the medicine audit system shown in FIG. 2. Here, in FIG. 3, illustration of the network 40, the dedicated computer 50 and the network interface 52 shown in FIG. 2 is omitted.

The medicine audit device 10 includes a display unit 15, an operating unit 16 and a conveying unit 18. The medicine audit device 10 includes a system control unit. The system control unit comprehensively controls each unit of the medicine audit device 10. Here, illustration of the system control unit is omitted.

The display unit 15 displays various information relating to the medicine audit device 10. The display unit 15 includes the display device 14 shown in FIG. 1 and a display control unit. The display control unit converts the signals representing various information to be displayed on the display device 14 into display signals, and transmits the display signals to the display device 14. Here, illustration of the display control unit is omitted.

The operating unit 16 is also used as the display device 14 shown in FIG. 1. The signals input from the operating unit 16 are converted into signals to be transmitted to each unit by using the system control unit. The system control unit transmits signals to each unit based on the information input by using the operating unit 16.

The conveying unit 18 conveys the packaging film inserted from the insertion port 20 to the discharge port 22, shown in FIG. 1. In a conveying path of the packaging film, imaging devices and lighting devices are arranged. The conveying unit 18 includes a conveying mechanism and a conveying control unit.

The conveying mechanism supports and conveys the packaging film. The conveying control unit operates the conveying mechanism in response to command signals transmitted from the system control unit. Here, illustration of the conveying mechanism, the conveying control unit, and the system control unit is omitted.

The medicine audit device 10 includes an information acquiring unit 60. The information acquiring unit 60 acquires various information to be used for medicine audit.

Various information may include: a packaging film image that is a captured image of the packaging film including a plurality of medicine images; imaging condition information; lighting condition information; and prescription information. The medicine image is an image of each medicine extracted from the packaging film image. Details of the information acquiring unit 60 are described later.

The term "image" in this specification may include the meaning of image data or an image signal representing an image.

The medicine audit device 10 includes a processing unit 61 and a local database 64. The processing unit 61 includes a medicine type determining unit 62. The medicine type determining unit 62 refers to the local database 64 and uses various information acquired by using the information acquiring unit 60 to determine the type of medicines. The medicine type determining unit 62 transmits a signal indicating the determination result to the display unit 15. The display unit 15 causes the display device 14 to display the determination result.

The medicine type determining unit 62 transmits imaging condition information based on the packaging film image and the medicine images to the information acquiring unit 60. The information acquiring unit 60 receives the imaging condition information transmitted from the medicine type determining unit 62. The imaging condition information is described in detail later.

The local database 64 stores master information on medicines. The master information includes a medicine name of each medicine, a master image of each medicine, and attribute information on each medicine. The local database 64 can search for a master image and attribute information by using a medicine name as an index. Note that the local database 64 described in the embodiment corresponds to an example of the first master image storing unit.

The processing unit 61 includes a determination result correcting unit 66. The determination result correcting unit 66 adds identification information, such as a medicine name that an operator inputs by operating the operating unit 16, to the medicine image that is determined to be indeterminable in the medicine type determining unit 62.

The determination result correcting unit 66 may add identification information indicating indeterminability to the medicine image that is determined to be indeterminable. The determination result correcting unit 66 may be configured so as not to add the identification information to the medicine image that is determined to be indeterminable.

Note that the determination result correcting unit 66 described in the embodiment corresponds to an example of the associating unit that associates the medicine image and the identification information. The operating unit 16 described in the embodiment corresponds to an example of the identification information input unit. No addition of the identification information described in the embodiment corresponds to an example of no association of the identification information.

The medicine audit device 10 includes a medicine information transmitting unit 68. The medicine information transmitting unit 68 combines the medicine image determined to be indeterminable with the identification information such as a medicine name, imaging condition information and lighting condition information, as a set, and then, transmits the set to the server device 32 as medicine information. The medicine image to which the identification information is not added, is combined with the imaging condition information and the lighting condition information, as a set, and then, transmitted to the server device 32 as medicine information. Note that the server device 32 described in the embodiment corresponds to an example of the outside of the medicine audit device 10.

The imaging condition information includes position information on the medicine image. The position information on the medicine image may be acquired from the packaging film image. It is possible to correct distortion of the captured image by using the position information on the medicine. The imaging condition information may include medicine arrangement information. Examples of the medicine arrangement information may include information indicating that the medicine is tilted in a prescribed direction, and information indicating that the medicine is imaged in the state of overlapping with other medicines.

The lighting condition information may include information indicating the direction from which the medicine is lighted.

The server device 32 includes a medicine information acquiring unit 70, an image processing unit 72, and a master database 74. The medicine information acquiring unit 70 acquires medicine information transmitted from the medicine information transmitting unit 68 included in the medicine audit device 10. The server device 32 may acquire the medicine information from a plurality of medicine audit devices 10. The server device 32 aggregates information about the medicines having identical medicine names. The server device 32 updates the master database 74 based on the captured images of the medicines having the identical medicine names.

Among the medicine images determined to be indeterminable, the server device 32 adds identification information such as the medicine name to medicine images having no identification information and medicine images having identification information indicating indeterminability, so as to be usable for update of the master database 74.

The server device 32 includes the image processing unit 72. The image processing unit 72 performs correction processing on the captured image acquired from the medicine audit device 10 in consideration of information such as the imaging condition information and the lighting condition information. The server device 32 can update the master database 74 using the captured image subjected to the correction processing.

For example, the image processing unit 72 may perform processing, such as magnification, reduction, and rotation, on the captured image of the medicine. The image processing unit 72 may generate a composite image of captured images by composing an image imaged (captured) when the medicine is illuminated from any one direction and an image imaged when the medicine is illuminated from the other direction.

When composition processing is performed, captured images that are determined to be unmatched with other captured images in imaging condition information, lighting condition information, or the like, may be excluded from the targets of composition processing. The captured images with medicine names erroneously input, the captured images that are imaged in the state of overlapping with other medicines, and the captured images that are imaged at angles where it is difficult to recognize engraved marks and the like, may be excluded from the targets of composition.

The server device 32 can update the master database 74 with use of the captured image of a medicine subjected to the processing performed by the image processing unit 72.

The updating function of the master database 74 included in the server device 32 may be included in the medicine audit device 10. Specifically, the medicine audit device 10 may temporarily update the local database 64 based on the medicine image that is determined to be indeterminable, with use of the imaging condition information, the lighting condition information, and the like.

For the image processing unit 72, a learning model may be applied. The learning model learns the relationship between the captured image and the name of the medicine that is determined to be indeterminable in the medicine audit device 10, and updates the master database 74 based on the learning result.

The server device 32 performs periodical update of the master database 74 and periodically distributes update information on the master database 74 to the medicine audit device 10. The medicine audit device 10 updates the local database 64 based on the update information of the master database 74 transmitted from the server device 32.

Note that the medicine audit system 30 described in the embodiment corresponds to an example of the medicine collation system. The master database 74 described in the embodiment corresponds to an example of the second master image storing unit.

Each unit shown in FIG. 3 implements the functions of the medicine audit system by executing a prescribed program using hardware described below. As the hardware of each control unit, various types of processors can be applied. Examples of the processors may include a central processing unit (CPU) and a graphics processing unit (GPU). The CPU runs the program to function as various types of processing units.

The CPU is a general purpose processor. The GPU is a processor dedicated to image processing. As the hardware of the processor, an electrical circuit formed by combining electrical circuit elements such as semiconductor elements, is applied. Each control unit includes a ROM that stores program and the like and a RAM that is a working area or the like for various computations.

Two or more processors may be applied to one control unit. Two or more processors may be the processors of the same type or the processors of different types. Moreover, one processor may be applied to a plurality of control units.

[Detailed Description of Medicine Audit Device]
[Information Acquiring Unit]

Figure 4:
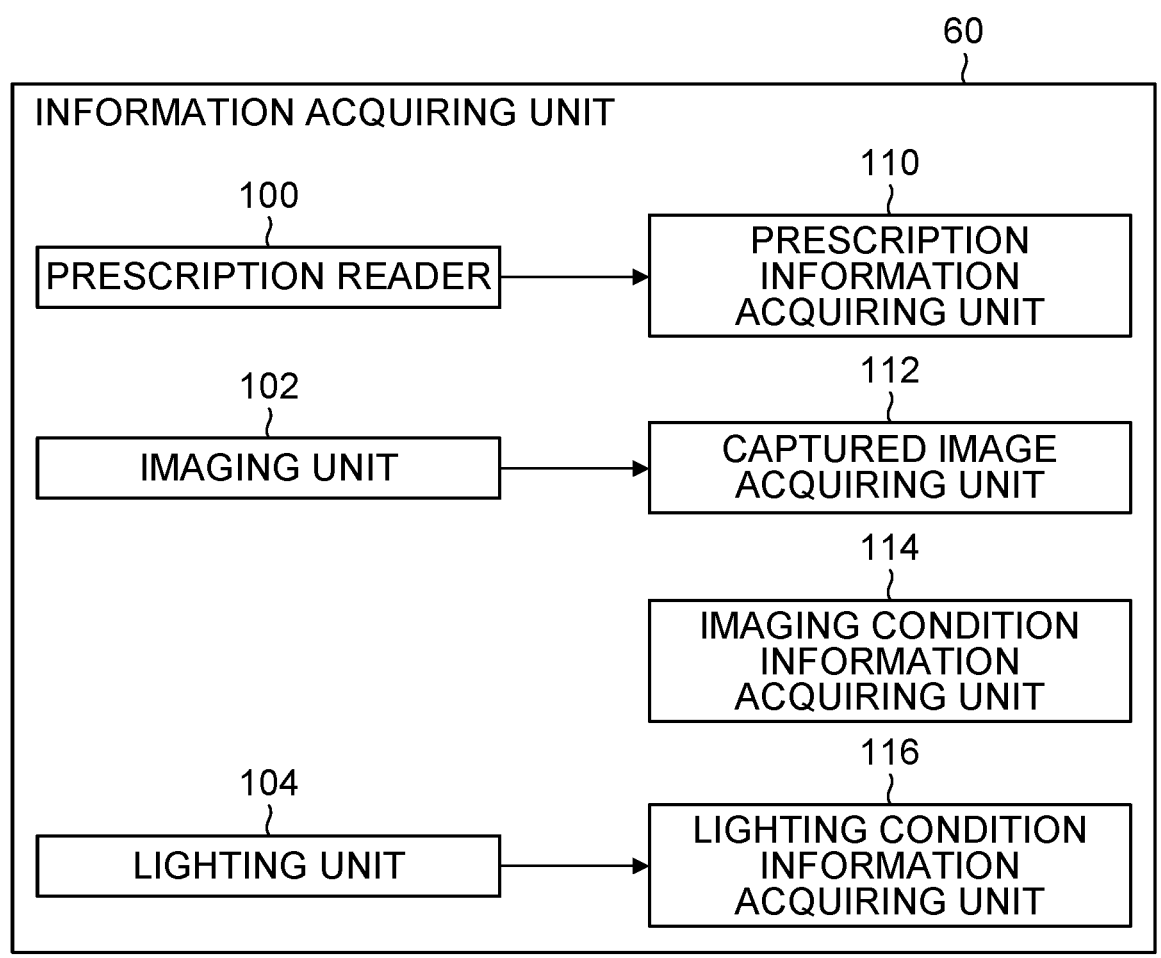
FIG. 4 is a functional block diagram of an information acquiring unit shown in FIG. 3.

FIG. 4 is a functional block diagram of the information acquiring unit shown in FIG. 3. The information acquiring unit 60 includes a prescription reader 100, an imaging unit 102, and a lighting unit 104. The prescription reader 100 acquires prescription information. As the prescription reader 100, an optical character recognition device may be applied. The optical character recognition device images a prescription and converts information such as the medicine name into character codes based on the prescription image. The optical character recognition device may be referred to as an OCR that stands for optical character recognition.

The prescription reader 100 transmits the information read from the prescription information to a prescription information acquiring unit 110. The prescription information acquiring unit 110 may include a prescription information storing unit that stores the prescription information.

The imaging unit 102 includes imaging devices and an imaging control unit. Here, in FIG. 4, illustration of the imaging devices is omitted. The imaging devices are designated by reference numerals 150 and 152 and illustrated in FIG. 5. Illustration of the imaging control unit is omitted.

Figure 9:
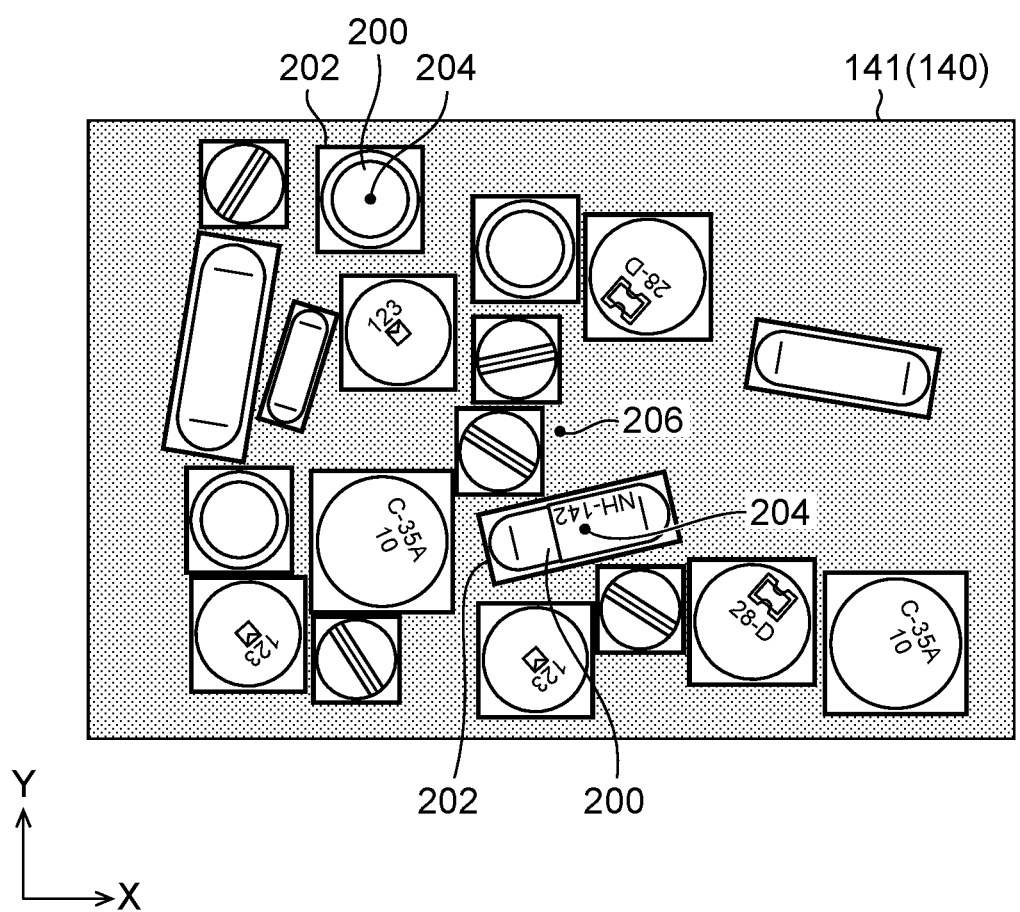
FIG. 9 is an explanatory view of medicine detection.

The imaging devices image (image-capture) medicines enclosed in the packaging film and generates a packaging film image. The packaging film image is illustrated in FIG. 9 with reference numeral 141. The imaging control unit controls the operation of the imaging devices. The imaging control unit transmits the packaging film image to a captured image acquiring unit 112. The captured image acquiring unit 112 may include a packaging film image storing unit that stores the packaging film images.

Note that the medicines enclosed in the packaging film described in the embodiment corresponds to an example of medicines to be collated. The captured image acquiring unit 112 described in the embodiment corresponds to an example of the medicine image acquiring unit.

The imaging condition information acquiring unit 114 acquires imaging condition information including information on the position of the medicine image in the packaging film image, from the medicine type determining unit 62 shown in FIG. 3. The imaging condition information acquiring unit 114 may include an imaging condition information storing unit that stores the imaging condition information.

Figure 5:
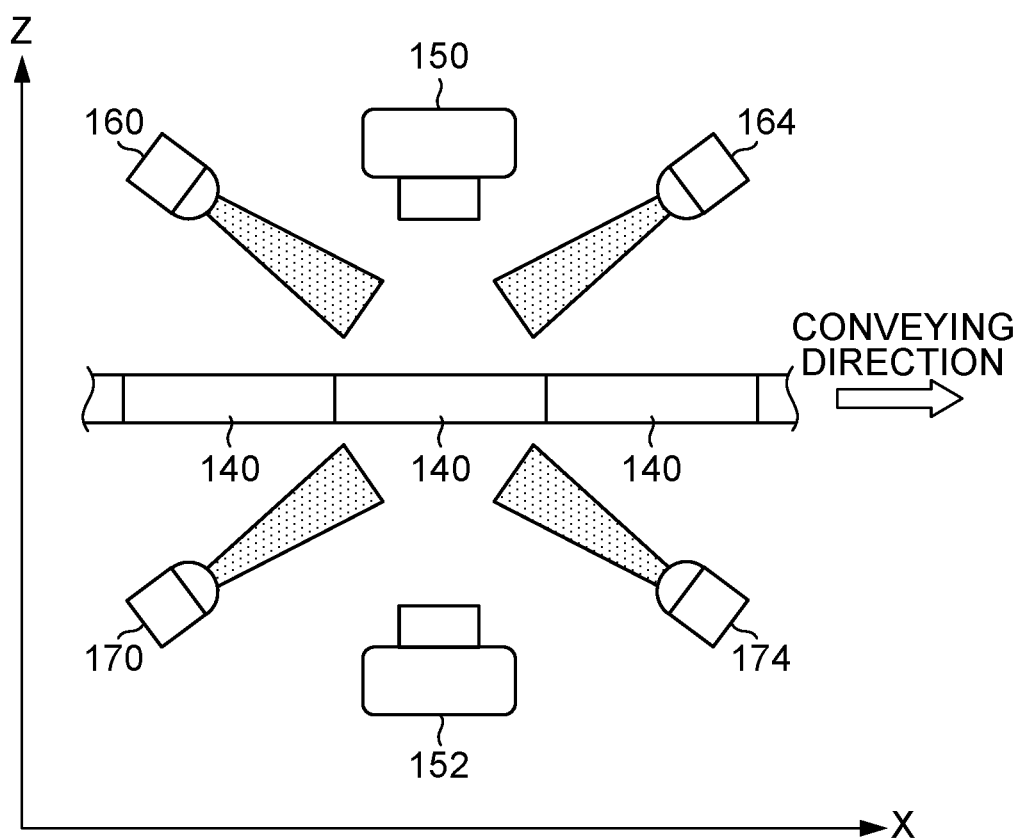
FIG. 5 is a schematic diagram showing an arrangement example of imaging devices and lighting devices.

The lighting unit includes lighting devices and a lighting control unit. Here, in FIG. 4, illustration of the lighting devices is omitted. The lighting devices are illustrated in FIG. 5 with reference numeral 160 and the like. Illustration of the lighting control unit is omitted. The lighting devices emit illumination light to the packaging film to be imaged. The lighting control unit controls the operation of the lighting devices. The lighting control unit transmits the lighting condition information to the lighting condition information acquiring unit 116.

The lighting condition information acquiring unit 116 acquires lighting condition information. The lighting condition information acquiring unit 116 may include a lighting condition information storing unit that stores the lighting condition information. The prescription information, the packaging film image, the imaging condition information and the lighting condition information are transmitted to the processing unit 61 shown in FIG. 3.

Arrangement Example of Imaging Devices and Lighting Devices

FIG. 5 is a schematic diagram showing an arrangement example of imaging devices and lighting devices. FIG. 5 shows a state of sequentially imaging of a plurality of packaging films 140 which are conveyed in a conveying direction. A reference character X shown in FIG. 5 designates the conveying direction of the packaging films 140. A reference character Z designates a vertical upward direction.

The plurality of packaging films 140 are conveyed in the conveying direction by using the conveying unit 18 shown in FIG. 3. On a conveying path of the packaging films 140, an upper imaging device 150 and a lower imaging device 152 are arranged. The upper imaging device 150 is arranged at a position to image (image-capture) the packaging film 140 from the upper side. The lower imaging device 152 is arranged at a position to image (image-capture) the packaging film 140 from the lower side.

As the upper imaging device 150 and the lower imaging device 152, cameras having imaging elements, such as CCD image sensors, can be applied. Here, CCD stands for charge coupled device.

Four lighting devices are arranged around an imaging region of the upper imaging device 150. Similarly, four lighting devices are arranged around an imaging region of the lower imaging device 152. The imaging regions of the upper imaging device 150 and the lower imaging device 152 include the entire part of one packaging film 140.

Here, the imaging region of the upper imaging device 150 represents an imaging visual field of the upper imaging device 150 having an optical axis in a fixed direction. The same is true for the lower imaging device 152. The upper imaging device 150 and the lower imaging device 152 are arranged at positions where their optical axes coincide with each other. Here, the optical axes of the upper imaging device 150 and the lower imaging device 152 are designated by reference numeral 151 and illustrated in FIG. 6.

FIG. 5 illustrates a first lighting device 160 and a third lighting device 164, out of four lighting devices corresponding to the upper imaging device 150. Similarly, as for the lighting devices corresponding to the lower imaging device 152, a fifth lighting device 170 and a seventh lighting device 174, out of the four lighting devices, are illustrated.

Figure 6:
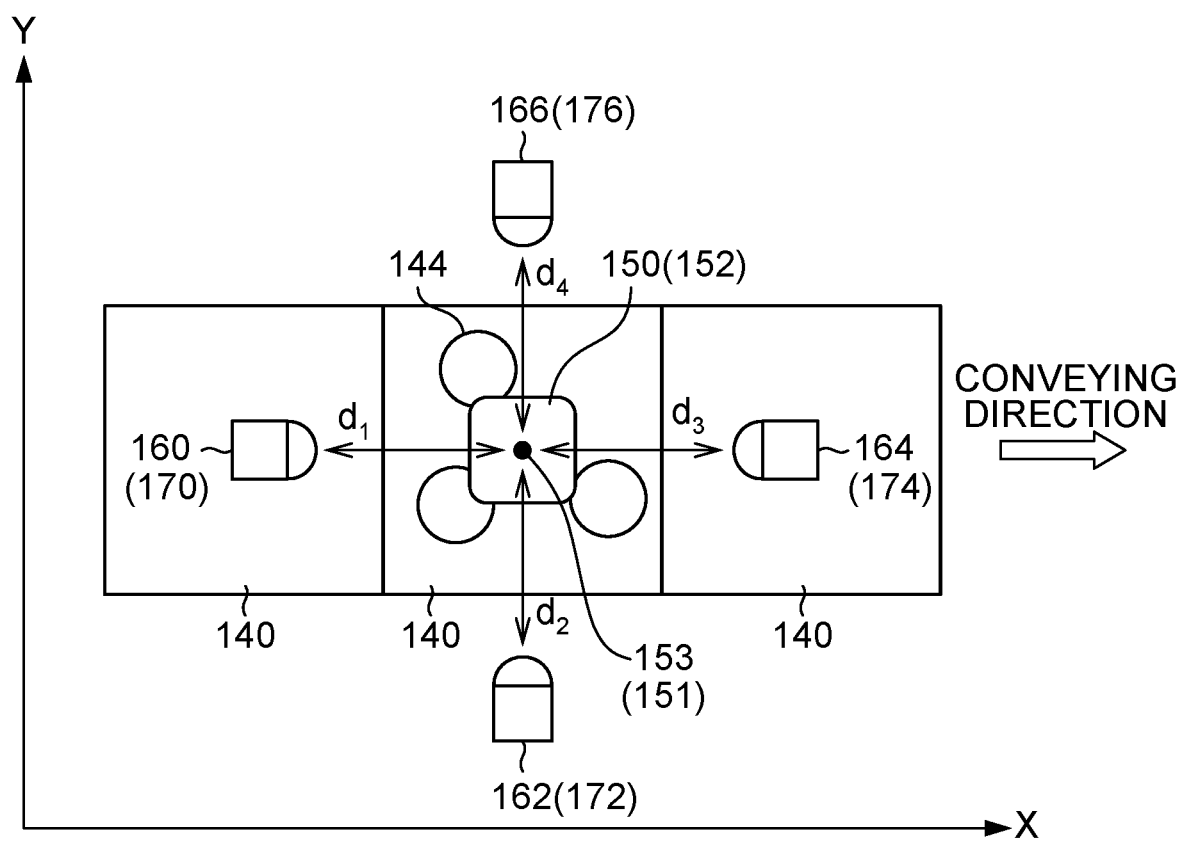
FIG. 6 is a schematic diagram showing an arrangement example of the lighting devices.

FIG. 6 is a schematic diagram showing an arrangement example of the lighting devices. FIG. 6 shows the diagram of FIG. 5 as viewed in an imaging direction of the upper imaging device 150. A reference numeral 144 designates a medicine enclosed in the packaging film 140. A reference character Y designates a width direction of the packaging film 140. The width direction of the packaging film 140 is a direction perpendicular to the conveying direction of the packaging film 140 and is a direction parallel to a conveying surface of the packaging film 140.

Note that the term "perpendicular" in this specification may include "substantially perpendicular" indicating the state of two directions which intersect in actuality though the operational effect same as the operational effect provided in the case of being perpendicular can be provided. Similarly, the term "parallel" may include "substantially parallel".

The first lighting device 160, a second lighting device 162, the third lighting device 164 and a fourth lighting device 166 are arranged at equal intervals along the circumference surrounding the imaging region of the upper imaging device 150. The center of the circumference surrounding the imaging region is a center position 153 of the imaging region. The optical axis 151 of the upper imaging device 150 passes through the center position 153 of the imaging region.

The first lighting device 160 and the third lighting device 164 are arranged symmetrically across the optical axis 151 of the upper imaging device 150 in the conveying direction of the packaging films 140. The second lighting device 162 and the fourth lighting device 166 are arranged symmetrically across the optical axis 151 of the upper imaging device 150 in the width direction of the packaging films 140.

A distance $d_1$ from the optical axis 151 of the upper imaging device 150 to an imaging surface of the first lighting device 160 is identical to a distance $d_3$ from the optical axis 151 of the upper imaging device 150 to the imaging surface of the third lighting device 164.

The distance $d_1$ from the optical axis 151 of the upper imaging device 150 to the imaging surface of the first lighting device 160 is also identical to a distance $d_2$ from the optical axis 151 of the upper imaging device 150 to the imaging surface of the second lighting device 162.

The distance $d_1$ from the optical axis 151 of the upper imaging device 150 to the imaging surface of the first lighting device 160 is further identical to a distance $d_4$ from the optical axis 151 of the upper imaging device 150 to the imaging surface of the fourth lighting device 166.

In other words, the first lighting device 160, the second lighting device 162, the third lighting device 164 and the fourth lighting device 166 are arranged at equal intervals from the optical axis 151 of the upper imaging device 150, and have relationship of $d_1=d_2=d_3=d_4$.

The fifth lighting device 170, a sixth lighting device 172, the seventh lighting device 174, and an eighth lighting device 176 are arranged at positions corresponding to the first lighting device 160, the second lighting device 162, the third lighting device 164 and the fourth lighting device 166, respectively.

The first lighting device 160 and the like may be configured such that a plurality of light emitting elements are arranged over the length corresponding to the entire length of the packaging films 140 in the width direction of the packaging film 140. The second lighting device 162 and the like may be configured such that a plurality of light emitting elements are arranged over the length corresponding to the entire length of the packaging film 140 in the conveying direction of the packaging film 140. Examples of the light emitting elements may include light emitting diodes (LED).

The first lighting device 160 and the like are controlled separately by the lighting control unit. The light quantity and on-off of the first lighting device 160 and the like may be controlled separately. The first lighting device 160 and the like are controlled in accordance with imaging timing of the upper imaging device 150. The fifth lighting device 170 and the like are controlled in accordance with imaging timing of the lower imaging device 152.

[Local Database]

FIG. 7 is a schematic diagram of the local database shown in FIG. 3. The local database 64 stores a medicine name 180, attribute information 182 and a master image 184 for each medicine. The master image 184 includes a front image 186 and a back image 188.

As the identification information, the medicine name 180 and the attribute information 182 may be applied. As the attribute information 182, a medicine code, a medicine type, a shape, a size, color, an engraved mark, printing and the like may be applied. Here, in FIG. 7, arbitrary character strings are illustrated as examples of the medicine name and the medicine code.

The front image 186 is an image generated by imaging the front surface of the medicine. The back image 188 is an image generated by imaging the back surface of the medicine. For example, the surface of the medicine which is marked and the surface of the medicine which is printed may be defined as the front surface. The front surface and the back surface are determined based on prescribed conditions.

[Medicine Type Determining Unit]

Figure 8:
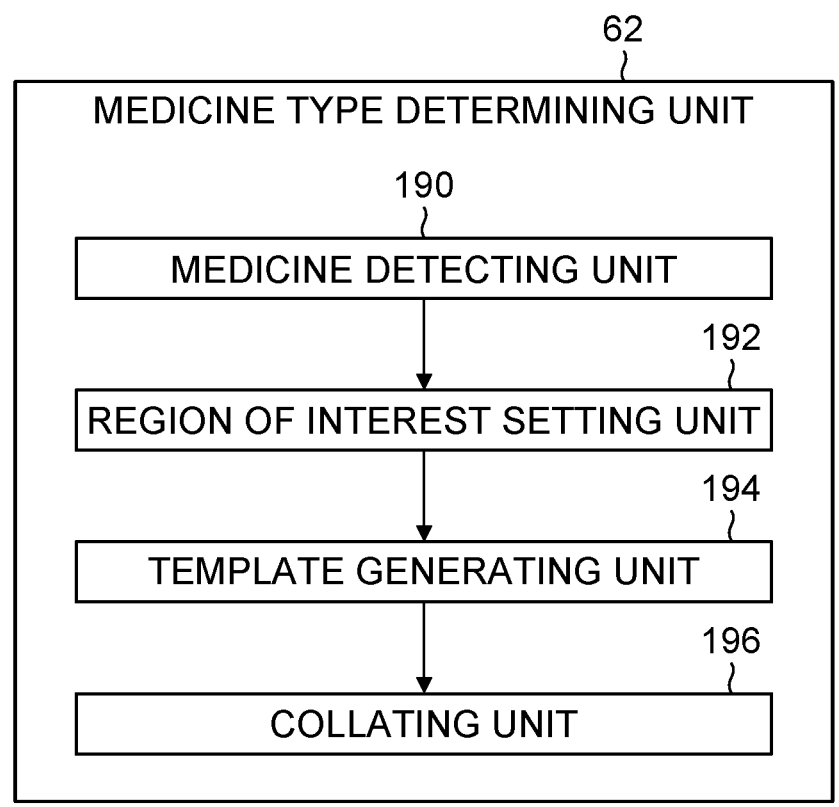
FIG. 8 is a functional block diagram of a medicine type determining unit shown in FIG. 3.

FIG. 8 is a functional block diagram of the medicine type determining unit shown in FIG. 3. The medicine type determining unit 62 includes a medicine detecting unit 190, a region of interest setting unit 192, a template generating unit 194, and a collating unit 196.

The medicine detecting unit 190 identifies regions of medicine images, which are images of respective medicines, from the packaging film image that is an overall image of the packaging film 140, and identifies the position of each medicine image. As the position information, coordinate values of two-dimensional coordinates set in the imaging region of the upper imaging device 150 and the imaging region of the lower imaging device 152 may be applied.

The medicine detecting unit 190 may perform image processing, such as magnifying, reducing, rotating, and adjusting brightness, on the medicine image based on the master image 184. Here, the packaging film image is designated by reference numeral 141 and illustrated in FIG. 9. The medicine images are designated by reference numeral 200 and illustrated in FIG. 9.

The region of interest setting unit 192 sets the region of interest for each medicine image. The region of interest includes features in the medicine image. The region of interest setting unit 192 calculates a distance from a center position of the packaging film image for each medicine image.

The region of interest setting unit 192 sets the shape of the region of interest for each medicine image in accordance with the distance from the center position of the packaging film image for each medicine image. As the center position of the packaging film image, a center position 153 of the imaging region shown in FIG. 6 is applied. Here, the center position of the packaging film image for each medicine image is designated by reference numeral 204 and illustrated in FIG. 9.

The template generating unit 194 generates a template for the master image 184 in accordance with the shape of the region of interest for each medicine image. The template generating unit 194 sets the position of the template in the master image 184 in accordance with the distance from the center position of the packaging film image, for each medicine image. The template includes the features of the medicine in the master image 184.

The collating unit 196 collates the region of interest in the medicine image with the template in the master image 184, for each medicine image. The collating unit 196 performs aligning processing between the region of interest and the template.

In the aligning processing, the collating unit 196 may perform processing, such as magnifying, reducing, and rotating, on at least one of the region of interest and the template. In the case where image processing is already applied to the medicine image, application of magnification processing and the like during aligning processing is not necessary. The collating unit 196 performs collation for all the medicine images included in the packaging film image.

The collating unit 196 compares the medicine image with the master image 184. The collating unit 196 mainly compares the region of interest in the medicine image with the template in the master image 184 to determine whether or not the region of interest and the template coincide. The collating unit 196 transmits the collation result to the determination result correcting unit 66 shown in FIG. 3.

The medicine type determining unit 62 performs collation for the packaging film image acquired from the upper imaging device 150 shown in FIG. 5 and the packaging film image acquired from the lower imaging device 152.

FIG. 9 is an explanatory view of medicine detection. The medicine detecting unit 190 shown in FIG. 8 sets, for the packaging film image 141 shown in FIG. 9, frames 202 encircling the entire medicine images 200 based on edge detection results of the medicine images 200, and sets the center positions of the respective frames 202 as the center positions 204 of the medicine images 200. The reference numeral 206 designates the center position of the packaging film image 141.

When setting the frames 202, the medicine detecting unit 190 may perform processing to remove low frequency components from the packaging film image 141 to emphasize the printing, engraved mark and the like on the medicines. The medicine detecting unit 190 may extract color information from the packaging film image 141, and use the color information to set the frames 202 for the packaging film image 141.

Figure 10:
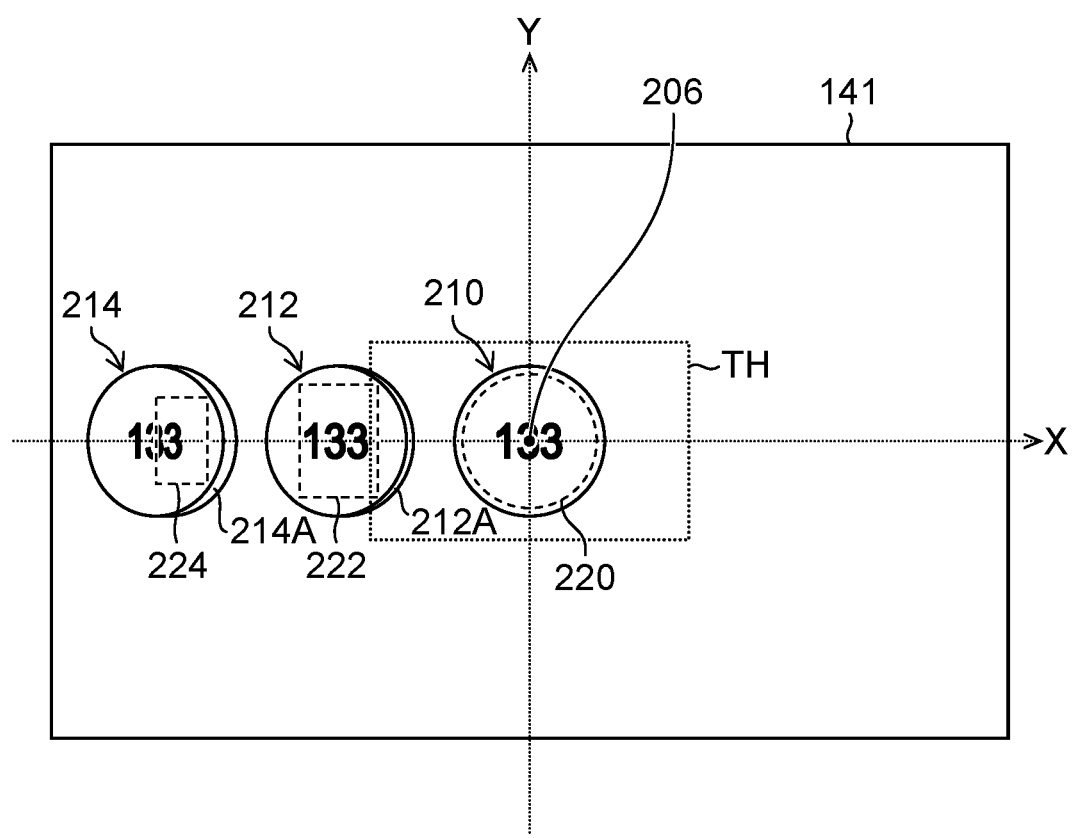
FIG. 10 is an explanatory view showing setting examples of a region of interest.

FIG. 10 is an explanatory view showing setting examples of the region of interest. FIG. 10 is a schematic view of the packaging film image 141. FIG. 10 shows a two-dimensional coordinate system with the center position 206 of the packaging film image 141 as an origin, the conveying direction of the packaging film 140 as an X direction, and the width direction of the packaging film 140 as a Y direction.

A distance of the medicine image 210 from the center position 206 of the packaging film image 141 is equal to or less than a threshold TH. The medicine image 210 has a region of interest 220 that is set to be similar in shape to the planar shape of the medicine image 210. In other words, a circular region of interest 220 is set for the medicine image 210.

Distances of a medicine image 212 and a medicine image 214 from the center position 206 of the packaging film image 141 are more than the threshold TH. For the medicine image 212, a rectangular region of interest 222 is set. For the medicine image 214, a rectangular region of interest 224 which is smaller than the region of interest 222 is set.

When the position of the medicine image 212 or the like is relatively distant from the center position 206 of the packaging film image 141, the medicine image 212 or the like is distorted from the shape of the medicine, and a lateral surface of the medicine appears in the packaging film image 141. The lateral surface of the medicine image 214 also appears. A reference numeral 212A designates a region of the medicine image 212 corresponding to the lateral surface of the medicine. The same applies to a reference numeral 214A.

When the region of interest 222 or the like is fixed in the same way as the region of interest 220, a region where distortion is generated and a region not necessary for collation are included in the region of interest 220 or the like. This can cause errors when the region of interest is collated with the template based on the master image that is free from distortion and without the lateral surface.

Accordingly, for each medicine image 212 or the like, the shape and size of the region of interest 222 or the like are set in accordance with the distance from the center position 206 of the packaging film image 141.

Figure 11:
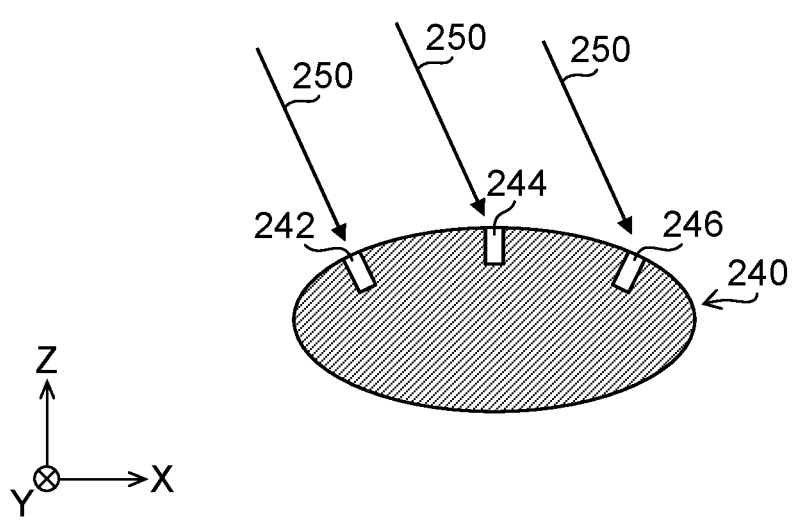
FIG. 11 is an explanatory view of the influence of illumination light.

FIG. 11 is an explanatory view of the influence of illumination light. FIG. 11 schematically illustrates the cross section of the medicine 240. An arrow line designated by reference numeral 250 represents illumination light. The medicine 240 has a three-dimensional structure with a constant thickness and a curved surface shape.

When the medicine 240 is imaged at a position away from the center position 153 of the imaging region shown in FIG. 6, the illumination light from the lighting device which is close to the medicine 240 shown in FIG. 11, among the four lighting devices such as the first lighting device 160, has stronger influence.

An engraved mark 242 on the medicine 240 receives the illumination light 250 from almost directly above. The engraved mark 242 forms almost no shadow. On the other hand, an engraved mark 244 and an engraved mark 246 receive illumination light 250 from inclined directions. The engraved mark 244 and the engraved mark 246 form shadows.

When the medicine 240 is imaged at the center position 153 of the imaging region, the images of the engraved mark 244 and the engraved mark 246 are clear, whereas the image of the engraved mark 242 is blurred. Collation using the medicine image having a blurred engraved mark 242 may cause collation error attributed to mismatch of engraved mark 242.

When setting the region of interest for the medicine images, it is possible to set the region of interest that does not include the regions that may be affected by the illumination light 250, such as blurriness in the image of the engraved mark 242.

[About Use of Lighting Condition Information]

In the case of setting the region of interest 220 or the like shown in FIG. 10 for the medicine images 200 shown in FIG. 9, lighting condition information can be used. Even in a case where medicines are imaged at the same position, the state of shadows may differ depending on the color, shape, and the like of the medicines. The medicine detecting unit 190 shown in FIG. 8 can use the lighting condition information such as the type of illumination light and the light quantity of the illumination light, to set the region of interest 220 or the like which is suitable for collation with the template in the master image 184.

[Display of Audit Result]

Figure 12:
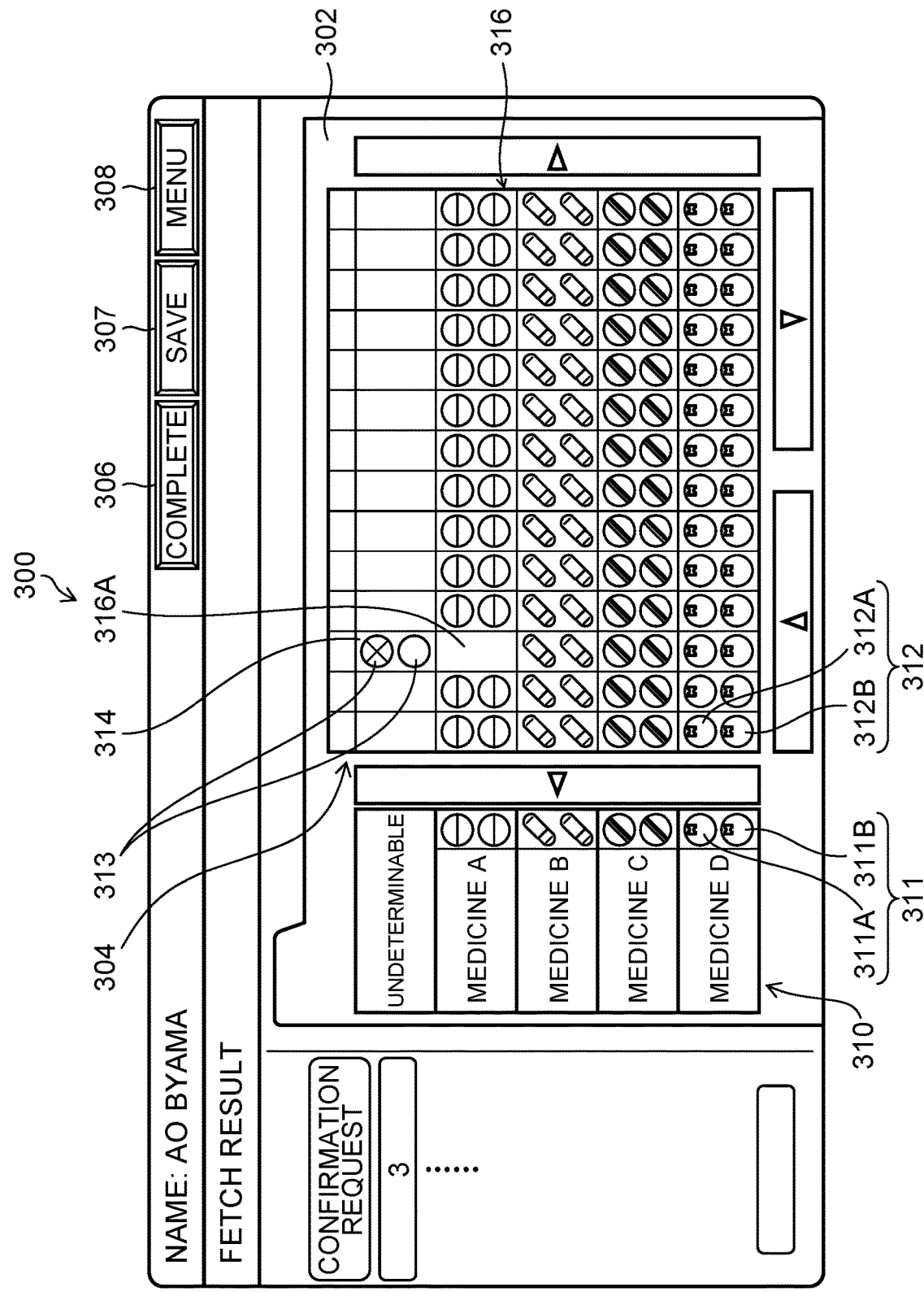
FIG. 12 is an explanatory view of an audit result display screen.

FIG. 12 is an explanatory view of an audit result display screen. The medicine audit device 10 uses the display device 14 to display an audit result. On an audit result display screen 300, an audit result 304 in a list format, in which medicine images 312 are arrayed for each master image 311, is displayed in an audit result area 302 for each of the packaging films 140.

The audit result display screen 300 displays a complete button 306, a save button 307 and a menu button 308. When the complete button 306 is operated, the medicine audit device 10 ends the audit result display screen 300.

When the save button 307 is operated, the medicine audit device 10 saves the audit result. When the menu button 308 is operated, the medicine audit device 10 uses the display device 14 to display the menu screen.

The audit result 304 includes a master image display field 310 which displays the master images 311. The master image display field 310 displays front images 311A of the master images 311 and back images 311B of the master images 311. The front image 311A and the back image 311B correspond to the front image 186 and the back image 188 shown in FIG. 7, respectively.

The audit result 304 includes a medicine image display field 316 which displays the medicine images 312. The medicine image display field 316 displays front images 312A of the medicine images 312 and back images 312B of the medicine images 312. The medicine images 312 are displayed such that an orientation of the medicine images 312 is the same as an orientation of the master images 311. The medicine image 312 corresponds to the medicine image 200 shown in FIG. 9.

The audit result 304 includes an indeterminable medicine display field 314, which displays a medicine image 313 of a medicine determined to be indeterminable. The medicine image display field 316 in the audit result 304 is empty when there is no medicine images 312 corresponding to the master images 311. A reference numeral 316A designates an empty medicine image display field 316.

The medicine image 313 which is determined to be indeterminable, may be generated because the master image 311 is not registered in the local database 64 shown in FIG. 3. The medicine image 313 which is determined to be indeterminable, may be generated due to a failure of collation between the medicine image 313 and the master image 311 under the influence of the imaging condition information, the lighting condition information and the like.

The medicine audit device 10 may use the display device 14 to display the audit result correction screen. An operator can correct the audit result by using the audit result correction screen. Examples of audit result correction may include an example of adding identification information, such as the medicine name, to the medicine image 313 of the medicine which is determined to be indeterminable.

[Correction of Audit Result]

Figure 13:
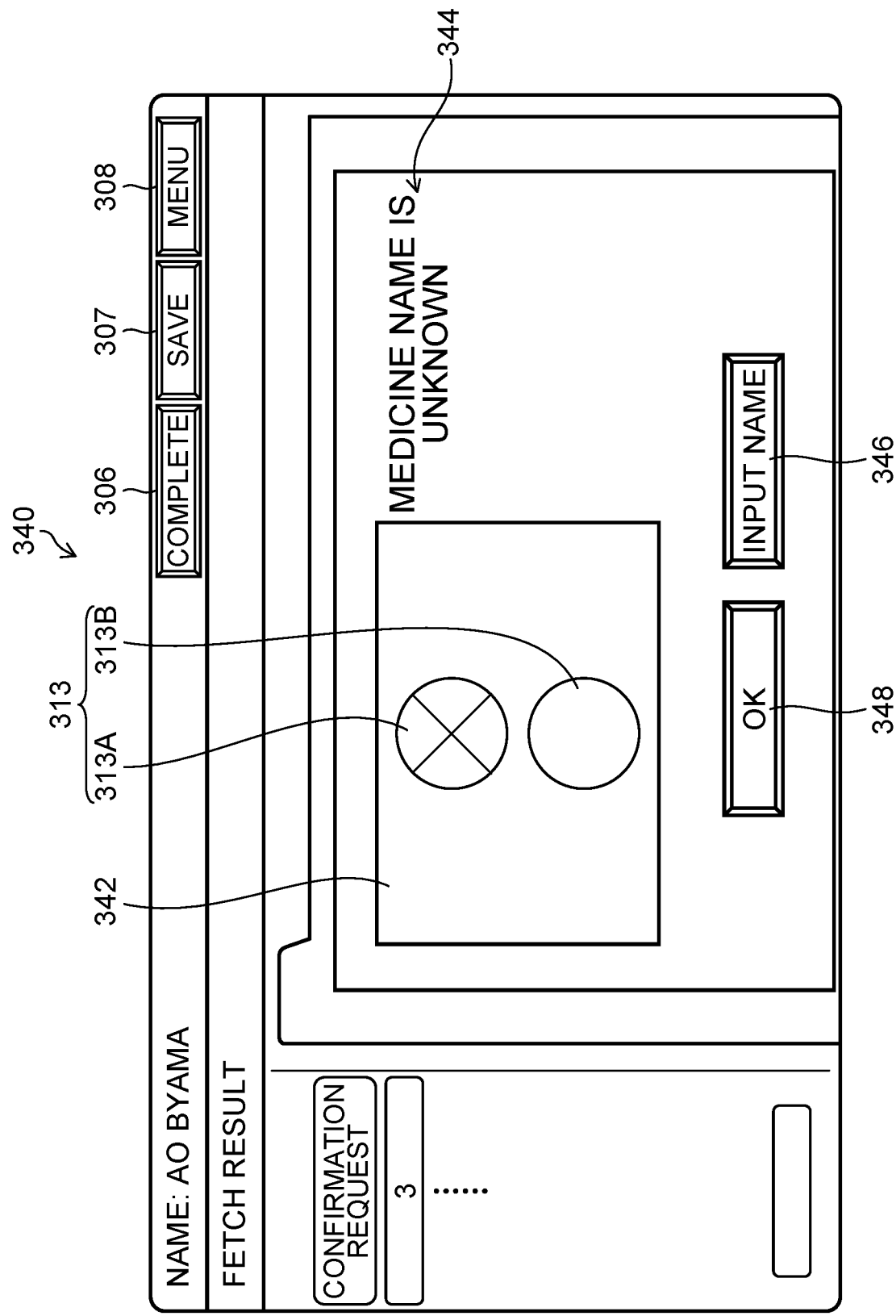
FIG. 13 is an explanatory view of an audit result correction screen.

FIG. 13 is an explanatory view of the audit result correction screen. An audit result correction screen 340 includes a medicine image display area 342, a text information display area 344, a medicine name input button 346 and an OK button 348.

The medicine image display area 342 displays the medicine image 313 which is determined to be indeterminable. The medicine image display area 342 displays front images 313A and back images 313B, as the medicine image 313.

The text information display area 344 displays text information indicating that the medicine name is unknown. The medicine name input button 346 is operated in the case of inputting the medicine name corresponding to the medicine image 313 displayed in the medicine image display area 342. The operator can input identification information such as the medicine name by using the operating unit 16 shown in FIG. 3.

The OK button 348 is operated in the case of not inputting the medicine name corresponding to the medicine image 313. When the operator operates the OK button 348, the medicine audit device 10 ends display of the audit result correction screen 340.

To the corrected audit result, imaging condition information on the medicine image 313 and lighting condition information on the medicine image 313 are added, and then the corrected audit result is transmitted to the server device 32 via the medicine information transmitting unit 68 shown in FIG. 3.

[Procedure of Medicine Management Method]

Figure 14:
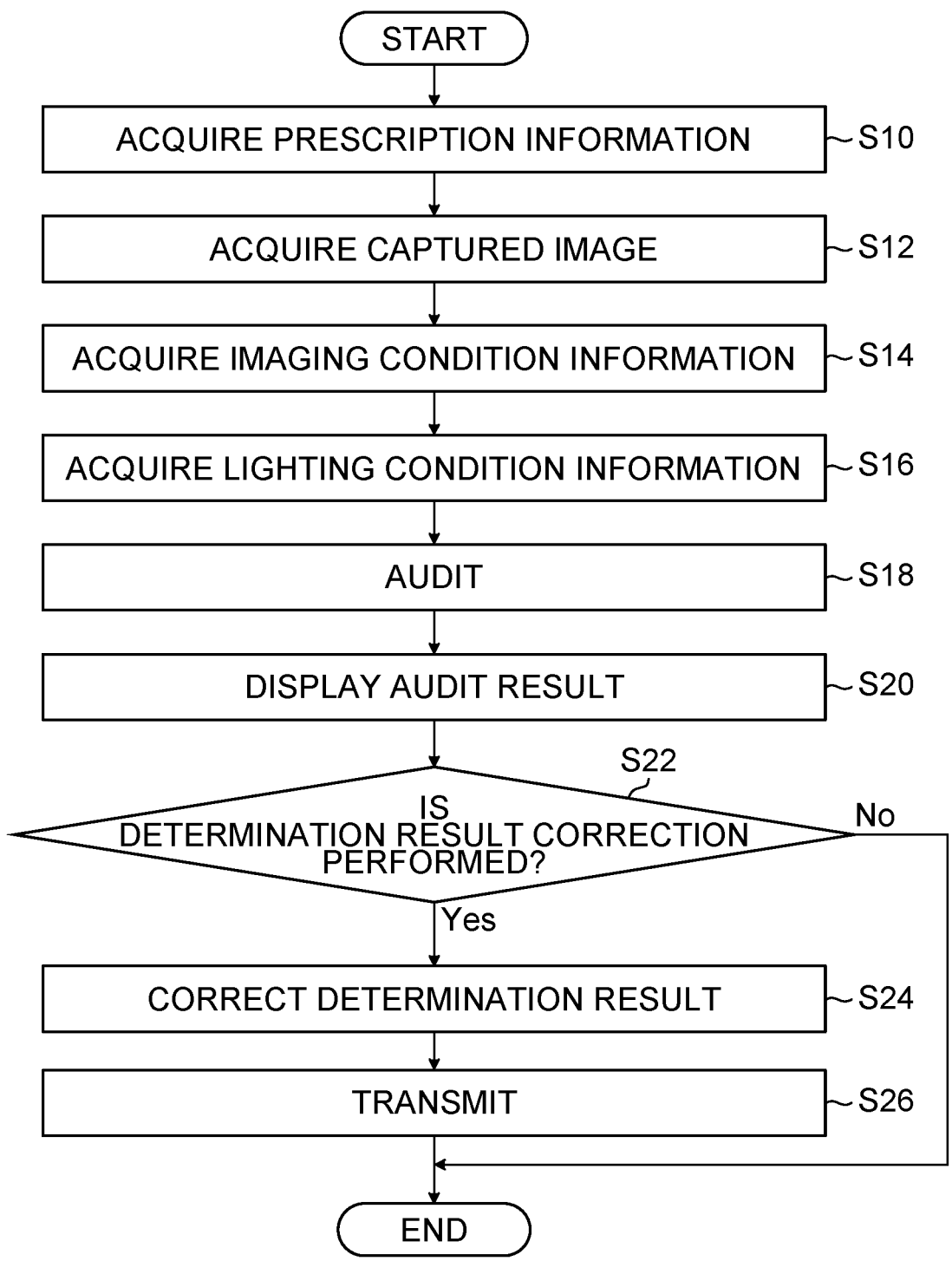
FIG. 14 is a flowchart showing a procedure of a medicine management method.

FIG. 14 is a flowchart showing the procedure of a medicine management method. In prescription information acquiring step S10, the prescription information acquiring unit 110 shown in FIG. 4 acquires prescription information. After prescription information acquiring step S10, the processing proceeds to captured image acquiring step S12.

In captured image acquiring step S12, the captured image acquiring unit 112 shown in FIG. 4 acquires the packaging film image 141 shown in FIG. 9. After captured image acquiring step S12, the processing proceeds to imaging condition information acquiring step S14. Note that captured image acquiring step S12 described in the embodiment corresponds to an example of the medicine image acquiring step.

In imaging condition information acquiring step S14, the imaging condition information acquiring unit 114 acquires imaging condition information. The imaging condition information includes information on a distance from the center position 206 of the packaging film image 141 for each medicine image 200. After imaging condition information acquiring step S14, the processing proceeds to lighting condition information acquiring step S16.

In lighting condition information acquiring step S16, the lighting condition information acquiring unit 116 acquires lighting condition information from the lighting unit 104. After lighting condition information acquiring step S16, the processing proceeds to audit step S18. Here, lighting condition information acquiring step S16 may be performed before imaging condition information acquiring step S14, or may be performed in parallel with imaging condition information acquiring step S14.

In audit step S18, the medicine type determining unit 62 shown in FIG. 3 performs audit. After audit step S18, the processing proceeds to audit result display step S20. In audit result display step S20, the medicine audit device 10 uses the display device 14 to display the audit result. After audit result display step S20, the processing proceeds to determination result correction determining step S22. Note that audit step S18 described in the embodiment corresponds to an example of the collating step.

In determination result correction determining step S22, the determination result correcting unit 66 determines whether or not to perform correction for the medicine that is determined to be indeterminable. When the determination result correcting unit 66 determines not to perform correction of the determination result in determination result correction determining step S22, No is determined. When No is determined, prescribed end processing is performed, and the medicine audit device 10 ends the medicine management method.

On the other hand, when the determination result correcting unit 66 determines to perform correction of the determination result in determination result correction determining step S22, Yes is determined. When Yes is determined, the processing proceeds to determination result correcting step S24.

In determination result correcting step S24, the determination result correcting unit 66 adds identification information such as the medicine name, to the medicine image 313 that is determined to be indeterminable. Determination result correcting step S24 may perform a determination result correction storing step that stores the corrected determination result. After determination result correcting step S24, the processing proceeds to transmitting step S26. Note that determination result correcting step S24 described in the embodiment corresponds to an example of the associating processing step.

In transmitting step S26, the medicine information transmitting unit 68 transmits to the server device 32 the medicine image 313 that is determined to be indeterminable shown in FIG. 13, the identification information on the medicine image 313 added to the medicine image 313, the imaging condition information on the medicine image 313, and the lighting condition information on the medicine image 313 as a set.

After transmitting step S26, the prescribed end processing is performed, and the medicine audit device 10 ends the medicine management method.

It is also possible to implement an aspect in which when No is determined in determination result correction determining step S22, the processing proceeds to determination result correcting step S24. In such an aspect, in determination result correcting step S24, the determination result correcting unit 66 does not add the identification information to the medicine images that are determined to be indeterminable, and in transmitting step S26, the medicine information transmitting unit 68 transmits the medicine images to the server device 32.

In determination result correcting step S24, the determination result correcting unit 66 may add identification information indicating indeterminability, to the medicine images that are determined to be indeterminable. In transmitting step S26, the medicine information transmitting unit 68 transmits the medicine images to which the identification information indicating indeterminability is added, to the server device 32.

Example of Application to Program Invention

It is possible to configure a program which causes a computer to implement the function of each unit in the medicine audit device 10 and the function of each step in the medicine management method according to the embodiment. For example, it is possible to configure a program which causes a computer to implement an information acquiring function corresponding to the information acquiring unit 60, a medicine type determining function corresponding to the medicine type determining unit 62, a determination result correcting function corresponding to the determination result correcting unit 66, and a medicine image transmitting function corresponding to the medicine information transmitting unit.

Note that the information acquiring function described in the embodiment corresponds to an example of the medicine image acquiring function. The medicine type determining function described in the embodiment corresponds to an example of the collating function. The determination result correcting function described in the embodiment corresponds to an example of the associating processing function.

[Operational Effects]

The medicine audit device 10, the medicine audit system 30, and the medicine management method according to the embodiment can provide the following operational effects.

[1]

The determination result correcting unit 66 adds identification information including the medicine name, to the medicine image 313 that is determined to be indeterminable. The medicine information transmitting unit 68 transmits to the server device 32, the medicine image 313 and the medicine name as a set. As a result, the server device 32 can update the master database 74 by using the medicine image 313 and the medicine name.

[2]

The medicine information transmitting unit 68 further adds imaging condition information to the medicine image 313, and transmits the medicine image 313, the medicine name, and the imaging condition information to the server device 32, as a set. This allows the server device 32 to correct the medicine image 313 by using the imaging condition information, and the like.

[3]

The medicine information transmitting unit 68 further adds lighting condition information to the medicine image 313, and transmits the medicine image 313, the medicine name, and the lighting condition information to the server device 32, as a set. This allows the server device 32 to correct the medicine image 313 by using the lighting condition information, and the like.

[4]

The server device 32 periodically transmits update information to the local database 64 of the client system 34 based on the update of the master database 74. As a result, it is expected to enhance the accuracy of audit in the medicine audit device 10 included in the client system 34.

[5]

The medicine audit device 10 updates the local database 64 by using the medicine image 313 and the medicine name. This makes it possible to reduce the possibility of being indeterminable, and an enhanced accuracy of audit is expected.

In the present embodiment, examples of medicine audit based on the prescription information have been described. However, the medicine audit device 10 and the medicine management method according to the present embodiment are applicable to the discrimination that determines the type or the like of a target medicine without using the prescription information.

Suitable modifications, additions, and deletion of component members in the above-described embodiment of the present invention are possible without departing from the spirit of the present invention. There is no intention to limit the invention to the embodiment disclosed, but on the contrary, the invention is to cover all variations made by a person with ordinary skill in the art within a technical idea of the present invention.

REFERENCE SIGNS LIST

10 Medicine audit device
12 Main body
14 Display device
16 Operating unit
18 Conveying unit
20 Insertion port
22 Discharge port
30 Medicine audit system
32 Server device
34 Client system
40 Network
50 Dedicated computer
52 Network interface
54 Receipt computer
60 Information acquiring unit
61 Processing unit
62 Medicine type determining unit
64 Local database
66 Determination result correcting unit
68 Medicine information transmitting unit
70 Medicine information acquiring unit
72 Image processing unit
74 Master database
100 Prescription reader
102 Imaging unit
104 Lighting unit
110 Prescription information acquiring unit
112 captured image acquiring unit
114 Imaging condition information acquiring unit
116 Lighting condition information acquiring unit
140 Packaging film
141 Packaging film image
150 Upper imaging device
152 Lower imaging device
153 Center position of imaging region
160 First lighting device
162 Second lighting device
164 Third lighting device
166 Fourth lighting device
170 Fifth lighting device
172 Sixth lighting device
174 Seventh lighting device
176 Eighth lighting device
180 Medicine name
182 Attribute information
184 Master image
186 Front image of master image
188 Back image of master image
190 Medicine detecting unit
192 Region of interest setting unit
194 Template generating unit
196 Collating unit
200 Medicine image
202 Frame
204 Center position of medicine image
206 Center position of packaging film image
210 Medicine image
212 Medicine image
212A Lateral surface
214 Medicine image
214A Lateral surface
220 Region of interest
222 Region of interest
224 Region of interest
240 Medicine
250 Illumination light
300 Audit result display screen
302 Audit result area
306 Complete button
307 Save button
308 Menu button
310 Master image display field
311 Master image
311A Front image of master image
311B Back image of master image
313 Medicine image
313A Front image of medicine image
313B Back image of medicine image
314 Undeterminable medicine display field
316 Medicine image display field
316A Empty medicine image display field
340 Audit result correction screen
342 Medicine image display area
344 Text information display area
346 Medicine name input button
348 OK button
S10 to S26 Each step of medicine management method

What is claimed is:

1. A medicine collation system, comprising:
a server device including a master database configured to store a master image; and
a plurality of client systems, each of the client systems including a medicine collation device configured to compare a medicine image with the master image,
wherein the medicine collation device includes:
a first master image storage configured to store the master image provided by the master database; and
a processor configured to:
acquire the medicine image generated by imaging a medicine to be collated;
perform collation of the acquired medicine image, with the master image stored in the first master image storage;
associate the medicine image collated in the collation, with identification information on the medicine image; and
transmit the medicine image and the associated identification to the server device,
wherein the server device is configured to transmit update information on the master database to the medicine collation device when updating the master database,
wherein the processor in the medicine collation device is configured to update the first master image storage according to the update information on the master database transmitted from the server device.

2. The medicine collation system according to claim 1, wherein the processor in the medicine collation device is configured to associate the medicine image that is determined to be indeterminable in the collation, with the identification information.

3. The medicine collation system according to claim 2, wherein the processor in the medicine collation device is further configured to:
input the identification information on the medicine image; and
associate the identification information on the input medicine image, with the medicine image.

4. The medicine collation system according to claim 2, wherein processor in the medicine collation device is configured to associate the medicine image that is determined to be indeterminable in the collation, with the identification information indicating indeterminability.

5. The medicine collation system according to claim 2, wherein the processor in the medicine collation device is configured to update the master image stored in the first master image storage, by using the medicine image that is determined to be indeterminable in the collation and the identification information associated with the medicine image.

6. The medicine collation system according to claim 1, wherein the processor in the medicine collation device is further configured to:
   acquire imaging condition information on the medicine image; and
   associate the medicine image with the imaging condition information.

7. The medicine collation system according to claim 1, wherein the processor in the medicine collation device is further configured to:
   acquire lighting condition information on the medicine image, the lighting condition information including at least one of a type of illumination light and light quantity of the illumination light; and
   associate the medicine image with the lighting condition information.

8. The medicine collation system according to claim 1, wherein the processor in the medicine collation device is configured to transmit the medicine image that is not associated with the identification information, to the server device.

9. The medicine collation system according to claim 8, wherein the processor in the medicine collation device is configured does not to associate the medicine image that is determined to be indeterminable, with the identification information.

10. The medicine collation system according to claim 1, wherein the server device is configured to update the master image stored in the master database by using the medicine image and the identification information corresponding to the medicine image that are transmitted from the medicine collation device.

11. The medicine collation system according to claim 1, wherein the server device is communicably connected each of the client systems via a network.

12. A medicine management method in a medicine collation system comprising: a server device including a master database configured to store a master image; and a plurality of client systems, each of the client systems including a medicine collation device configured to compare a medicine image with the master image, wherein the medicine collation device includes a processor and a first master image storage configured to store the master image provided by the master database, the method, comprising:
   by the processor in the medicine collation device, acquiring the medicine image generated by imaging medicine to be collated;
   by the processor in the medicine collation device, collating the acquired medicine image with the master image of the medicine stored in the first master image storage;
   by the processor in the medicine collation device, associating the medicine image collated in the collating with identification information on the medicine image;
   by the processor in the medicine collation device, transmitting the medicine image and the associated identification information to an outside the server device;
   by the server device, transmitting update information on the master database to the medicine collation device when updating the master database; and
   by the processor in the medicine collation device, updating the first master image storage according to the update information on the master database transmitted from the server device.

* * * * *